United States Patent [19]

Lerman et al.

[11] Patent Number: 5,782,882
[45] Date of Patent: Jul. 21, 1998

[54] SYSTEM AND METHOD FOR ADMINISTERING TRANSCUTANEOUS CARDIAC PACING WITH TRANSCUTANEOUS ELECTRICAL NERVE STIMULATION

[75] Inventors: David J. Lerman; Richard C. Myers, both of McMinnville, Oreg.

[73] Assignee: Hewlett-Packard Company, Palo Alto, Calif.

[21] Appl. No.: 892,621

[22] Filed: Jul. 14, 1997

Related U.S. Application Data

[63] Continuation of Ser. No. 565,803, Nov. 30, 1995, abandoned.

[51] Int. Cl.[6] .................................................. A61N 1/36
[52] U.S. Cl. ............................ 607/10; 607/46; 607/63
[58] Field of Search ............................. 607/2, 9, 10, 46, 607/63, 70, 142

[56] References Cited

U.S. PATENT DOCUMENTS

| | | | |
|---|---|---|---|
| 4,759,368 | 7/1988 | Spanton et al. | 607/63 |
| 5,044,367 | 9/1991 | Endres et al. | 607/10 |
| 5,205,284 | 4/1993 | Freeman | 607/10 |
| 5,205,297 | 4/1993 | Montecalvo et al. | 128/798 |
| 5,370,665 | 12/1994 | Hudrlik | 607/15 |

FOREIGN PATENT DOCUMENTS

| | | | |
|---|---|---|---|
| 0518546 | 6/1992 | European Pat. Off. | A61N 1/362 |
| 4425546 | 1/1995 | Germany | A61N 1/362 |
| 2070435 | 11/1980 | United Kingdom | A61N 1/381 |

OTHER PUBLICATIONS

Mannheimer et al., "The effect of transcutaneous electrical nerve stimulation (TENS) on catecholamine metabolism during pacing–induced angina pectoris and the influence of naloxone", Elsevier Science, vol. 41, pp. 27–34, 1990.

Mannheimer et al., "Influence of Naloxone on the effects of high frequency transcutaneous electrical nerve stimulation in angina pectoris induced by arterial pacing", Br Heart J 1989; 62:36–42.

Shade, "Use of Transcutaneous Electrical Nerve Stimulation for a Patient with a Cardiac Pacemaker," Physical Therapy, vol. 65, No. 2, Feb. 1985, pp. 206–208.

Chapter 5 of 1994 Textbook of Advanced Cardiac Life Support, published by American Heart Association, pp. 5–2 to 5–6.

Long, "Fifteen Years of Transcutaneous Electrical Stimulation for Pain Control," Steretact Funct Neurosurg 1991; 56:2–19.

Transcutaneous Electrical Nerve Stimulation For Pain Control, Szeto, et al.; 1983, pp. 14–18.

*Primary Examiner*—George Manuel
*Assistant Examiner*—Kennedy J. Schaetzle

[57] ABSTRACT

A transcutaneous cardiac pacing system has one or more cutaneous electrodes suitable for attachment to a human patient and a transcutaneous pacing system coupled to supply pacing pulses to the patient via the cutaneous electrodes. The pacing pulses are effective to stimulate cardiac activity in the patient. The transcutaneous cardiac pacing system also includes a transcutaneous electrical nerve stimulation system coupled to supply nerve stimulation pulses to the patient via the same electrodes. The nerve stimulation pulses are effective to mitigate any discomfort that the patient might experience from the transcutaneous pacing pulses. The system thereby provides effective and tolerable emergency cardiac pacing without introduction of intravenous drugs or sedation of the patient.

20 Claims, 5 Drawing Sheets

SYSTEM AND METHOD FOR ADMINISTERING TRANSCUTANEOUS CARDIAC PACING WITH TRANSCUTANEOUS ELECTRICAL NERVE STIMULATION

This is a continuation of application Ser. No. 08/565,803 filed on Nov. 30, 1995 now abandoned.

TECHNICAL FIELD

This invention relates to cardiac pacemaker systems and to methods for administering cardiac pacing. More particularly, this invention relates to transcutaneous cardiac pacemaker systems and methods.

BACKGROUND OF THE INVENTION

Cardiac pacemakers stimulate cardiac activity in a human patient by delivering periodic electrical pulses through electrodes to the patient's heart. The electrical pulses cause electrical depolarization and subsequent cardiac contraction to assist the heart in beating at a desired rhythm. There are many different varieties of cardiac pacemaker systems. In general, cardiac pacemaker systems are named according to the location of the electrodes and the pathway that the electrical stimulus travels to the heart. For example, a "transcutaneous" cardiac pacemaker system delivers pacing impulses to the heart through the patient's skin using cutaneous electrodes (i.e., electrodes externally attached to the skin of the patient). A "transvenous" pacemaker system uses electrodes mounted on catheters that are maneuvered through large central veins to the right ventricle or right atrium of the heart. Other example cardiac pacemaker systems include an "epicardial" pacing system (electrodes placed on the surface of the heart) and a "transesophageal" pacing system (electrodes located in the esophagus).

This invention concerns the transcutaneous class of cardiac pacemaker systems. Transcutaneous pacing is commonly used in emergency medicine for immediate treatment of unstable bradycardia, a condition in which the heart is beating too slowly and/or irregularly. Since the electrodes are attached externally to the skin, the transcutaneous pacing can be applied immediately to a heart troubled patient without intervention, and thereby serve as a therapeutic bridge until a transvenous pacemaker can be established under more controlled circumstances. The use of transcutaneous pacing for emergency cardiac pacing is described in more detail in Chapter 5 of the 1994 Textbook of Advanced Cardiac Life Support, published on behalf of the American Heart Association. This chapter is hereby incorporated by reference.

One of the drawbacks with transcutaneous pacing is that patients may experience discomfort. More specifically, the discomfort is in the form of a muscular skeletal pain induced from electrical skin and muscle stimulation. Depending upon the patient's own tolerance level, this discomfort might range from moderate and tolerable to severe and intolerable.

Previous solutions to alleviate this muscular skeletal pain include use of intravenous drugs for analgesia and sedation. However, the introduction of drugs can mask or worsen the underlying pathophysiology of the patient. Additionally, use of intravenous drugs raises a risk of infection and requires a trained person to administer the IV.

One aspect of this invention is to provide a transcutaneous cardiac pacing system which mitigates the muscular skeletal pain without use of drugs or sedation.

SUMMARY OF THE INVENTION

According to one aspect of this invention, a transcutaneous cardiac pacing system has a set of cutaneous electrodes suitable for attachment to a human patient and a transcutaneous pacing system coupled to supply pacing pulses to the patient via the cutaneous electrodes. The pacing pulses are effective to stimulate cardiac activity in the patient. As an example, the pacing pulses are applied at a rate of up to 180 pulses per minute, whereby each pacing pulse has a duration of approximately 18–20 ms and an amplitude of approximately 10–200 mA.

The transcutaneous cardiac pacing system also includes a transcutaneous electrical nerve stimulation system coupled to supply nerve stimulation pulses to the patient via the same electrodes (although a separate set of electrodes may be used). The nerve stimulation pulses are effective to mitigate discomfort that the patient might experience from the pacing pulses. For example, the nerve stimulation pulses are applied at a rate of about 40 Hz, with each nerve stimulation pulse having a duration of approximately 100–500 gs and an amplitude of approximately 100 mA.

According to another aspect, a method for administering cardiac pacing comprises applying transcutaneous pacing to a patient to stimulate cardiac activity and applying transcutaneous electrical nerve stimulation to the patient concurrently with application of the transcutaneous pacing to mitigate discomfort in the patient.

Through the combined use of transcutaneous nerve stimulation pulses along with the pacing pulses, the system and method effectively provide transcutaneous cardiac pacing which alleviates the muscular skeletal pain without use of drugs or sedation.

DETAILED DESCRIPTION OF THE PREFERRED EMBODIMENT

Figure 1:
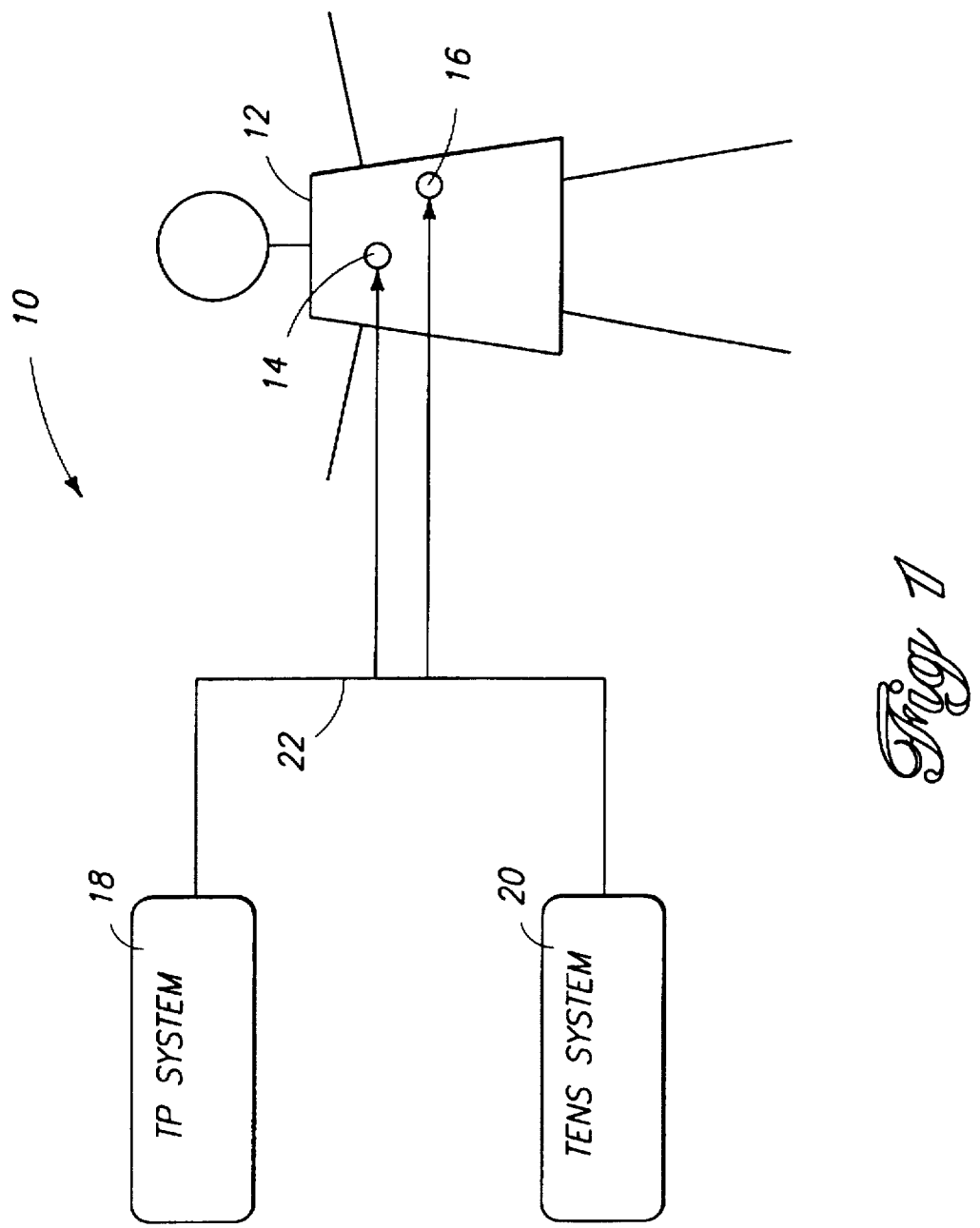
FIG. 1 is a diagrammatic illustration of a transcutaneous cardiac pacing system according to an aspect of this invention.

FIG. 1 shows a transcutaneous cardiac pacing system 10 for delivering electrical, heart stimulating pulses to a human patient 12. The transcutaneous cardiac pacing system 10 includes a set of two cutaneous electrodes 14 and 16 attached to the skin or cutaneous layer of the patient 12 at anatomically selected locations. To administer transcutaneous pacing, the electrodes 14 and 16 are conventionally placed at the anterior chest wall and back of the patient, or at the patient's sternum and apex of the heart.

The pacing system 10 has a transcutaneous pacing (TP) system 18 and a transcutaneous electrical nerve stimulation (TENS) system 20 connected to supply pulses to the electrodes 14 and 16 via a multi-conductor cable 22. The TP system 18 generates pacing pulses effective to stimulate cardiac activity in the human patient 12. In the preferred implementation, the TP system 18 produces pacing pulses that are applied to the human patient 12 at a rate of up to 180 pulses per minute. Each pacing pulse has a duration of approximately 18–20 ms and an amplitude of approximately 10–200 mA. In some patient's, the transcutaneous pacing pulses might cause mild or severe muscular skeletal discomfort.

To alleviate any discomfort, the TENS system 20 generates nerve stimulation pulses which are applied concurrently to the patient 12 along with the pacing pulses. In the preferred implementation, the TENS system 20 produces nerve stimulation pulses that are applied to the patient 12 at a rate of about 40 Hz. Each nerve stimulation pulse has a duration of approximately 100–500 µs and an amplitude of approximately 100 mA.

Accordingly, a method for administering cardiac pacing includes (1) applying transcutaneous pacing to a patient to stimulate cardiac activity and (2) concurrently applying transcutaneous electrical nerve stimulation to the patient to mitigate discomfort in the patient.

In the preferred implementation, the same set of electrodes 14 and 16 are used to administer both the pacing pulses and the nerve stimulation pulses. One suitable multipurpose electrode is disclosed in U.S. Pat. No. 5,205,297 to Montecalvo et al., which is hereby incorporated by reference. However, other types of electrodes may be used.

Figure 2:
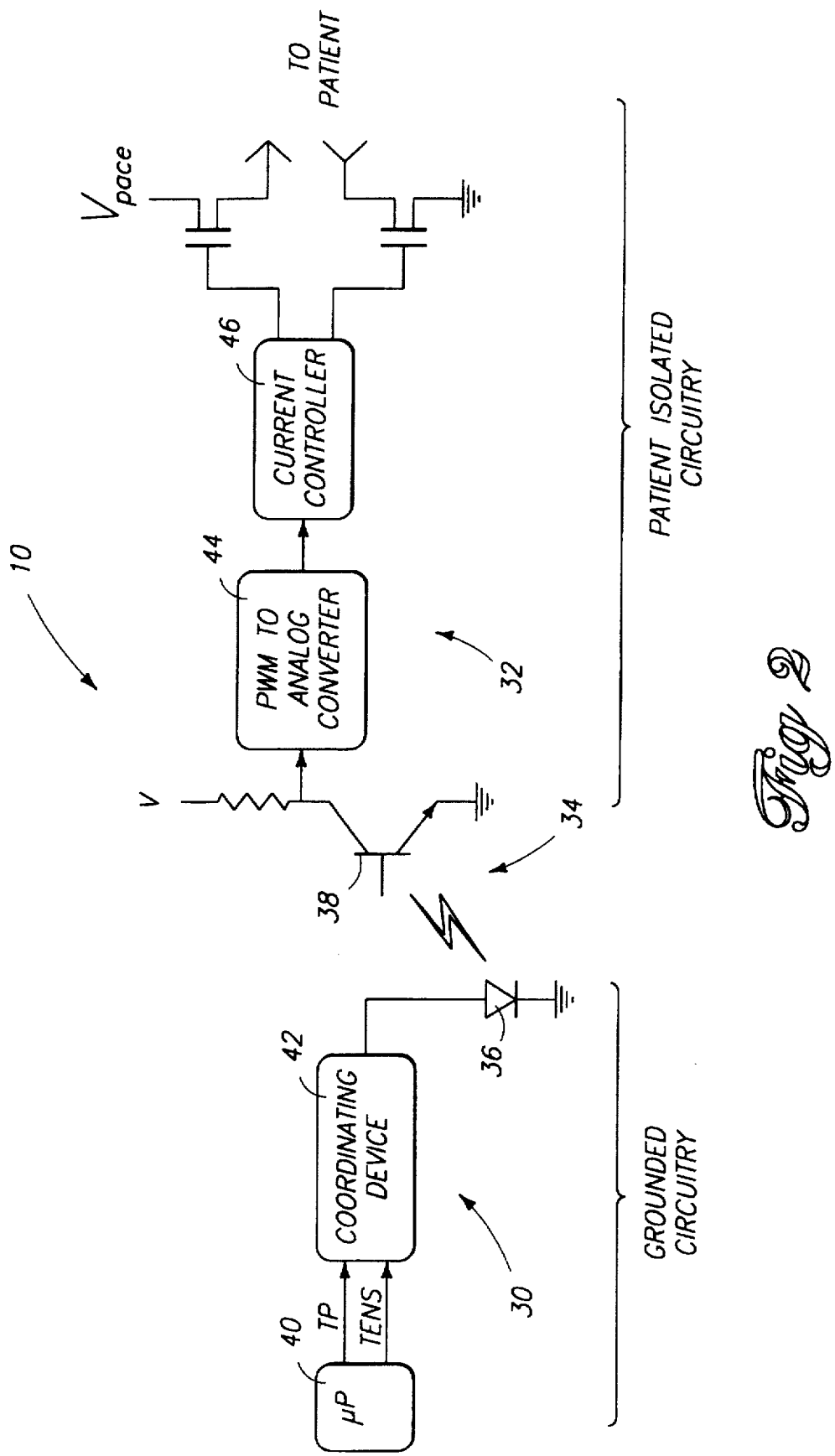
FIG. 2 is a block diagram of the transcutaneous cardiac pacing system.

FIG. 2 shows a more detailed block diagram of the transcutaneous cardiac pacing system 10. It includes a pacer circuit that has grounded circuitry 30 and patient-isolated circuitry 32 which floats at the patient's potential relative to ground. The grounded circuitry 30 and the patient-isolated circuitry 32 are electrically isolated from one another. An optical coupler 34 consisting of a photodiode 36 and a phototransistor 38 transfers control signals between the grounded circuitry and patient-isolated circuitry. Additionally, a power transformer (not shown) transfers power between the grounded and patient-isolated circuitry.

The pacer board 30 has a microprocessor 40 which generates both the TP signal and the TENS signal. In one implementation, the microprocessor 40 generates the TP signal and TENS signal as pulse width modulated (PWM) signals. A coordinating device 42 forms a single output signal consisting of both the PWM TP signal and the PWM TENS signal. In the preferred embodiment, the coordinating device 42 is a summing device which adds the TP and TENS signals. The combined PWM signal is transmitted across the optical isolation barrier via optical coupler 34 to the patient-based pacer circuit 32. The combined PWM signal is received at the phototransistor 38 and converted to an analog signal using PWM-to-analog converter 44. The analog signal is input to a current controller 46 which generates the corresponding pulse for output to the patient. The onset of the combined PWM signal conveys the start of a pulse, while the duty cycle of the combined PWM signal conveys the amplitude of the current to be delivered to the patient.

Figure 3:
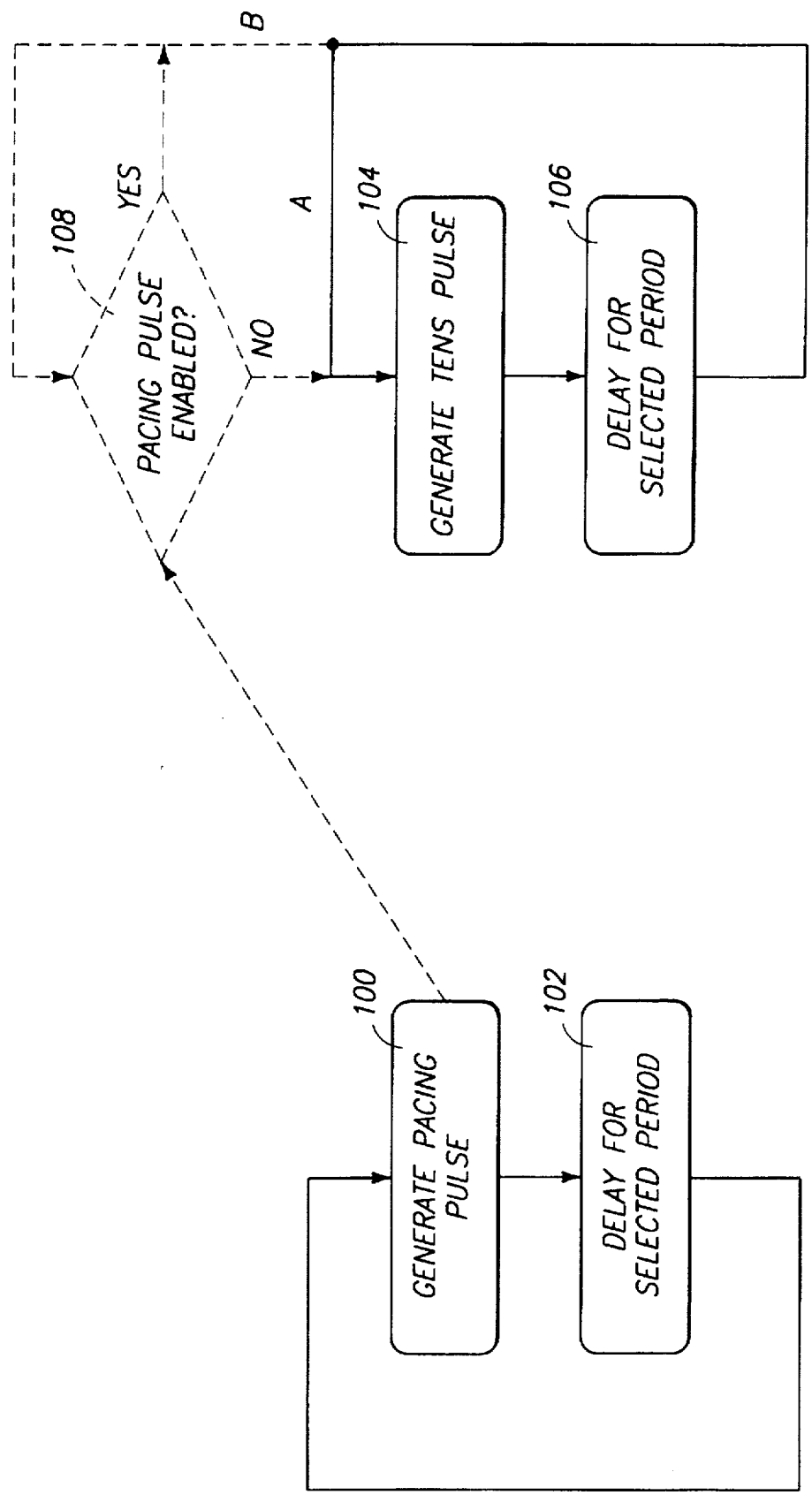
FIG. 3 is a flow diagram of steps performed by a microprocessor employed in the transcutaneous cardiac pacing system according to one implementation.

In this implementation, grounded circuitry 30 and patient-isolated circuitry 32 can be constructed using a commercially available defibrillator manufactured by Hewlett-Packard Company as product M1722A and sold under the name "Codemaster," which is modified to generate a TENS signal in addition to a TP signal, as shown in the flowchart of FIG. 3.

More specifically, the microprocessor 40 is programmed to perform the steps shown in FIG. 3. At step 100, the microprocessor generates and outputs a PWM pacing pulse. In the preferred embodiment, this pacing pulse has a duration of 18–20 ms. The microprocessor then delays a selected delay period before output of the next pacing pulse (step 102) to provide a rate of up to 180 pulses per minute. Meanwhile, and perhaps in parallel, the microprocessor generates and outputs a PWM nerve stimulation pulse, preferably having a duration of 100–500 µs (step 104). The microprocessor then pauses for a selected delay period before output of the next TENS pulse (step 106). The microprocessor can be programmed to dynamically alter the parameters of the pacing pulses and nerve stimulation pulses (e.g., intensity, pulse duration, amplitude modulation, frequency modulation, and wave shape) in response to input from an administering professional to effectively adapt to a patient's preference and comfort level.

In one construction, the microprocessor 40 can be programmed to perform the two loops independently of one another, whereby a pacing pulse and a TENS pulse can be generated and output simultaneously and then combined at the coordinating device 42 (FIG. 2). In a second construction, the microprocessor 40 can be programmed to disable generation of the shorter TENS signal during output of the longer pacing pulse. This is shown in FIG. 3 by the dashed flow lines, decision block 108, and a substitution of flow path B for flow path A. In the event that the microprocessor is outputting a pacing pulse at step 100, the decision block 108 prevents flow from continuing to the TENS generation loop. Conversely, when the microprocessor 40 is not generating a pacing pulse, step 108 permits generation of the TENS pulses during the period between pacing pulses. The microprocessor typically generates several TENS pulses between successive pacing pulses, the ratio of TENS pulses to pacing pulses depending upon the selected frequencies of the two pulses.

With reference again to FIG. 2, the patient-isolated circuitry 32 is based upon the patient-based circuit in the Codemaster, but modified to speed the response time of a current amplifier employed in the current controller 46. This modification enables the pacer circuit 34 to handle a comparatively shorter TENS pulse (i.e., 100–500 µs) in addition to the longer TP pulse (i.e., 18–20 ms).

Figure 4:
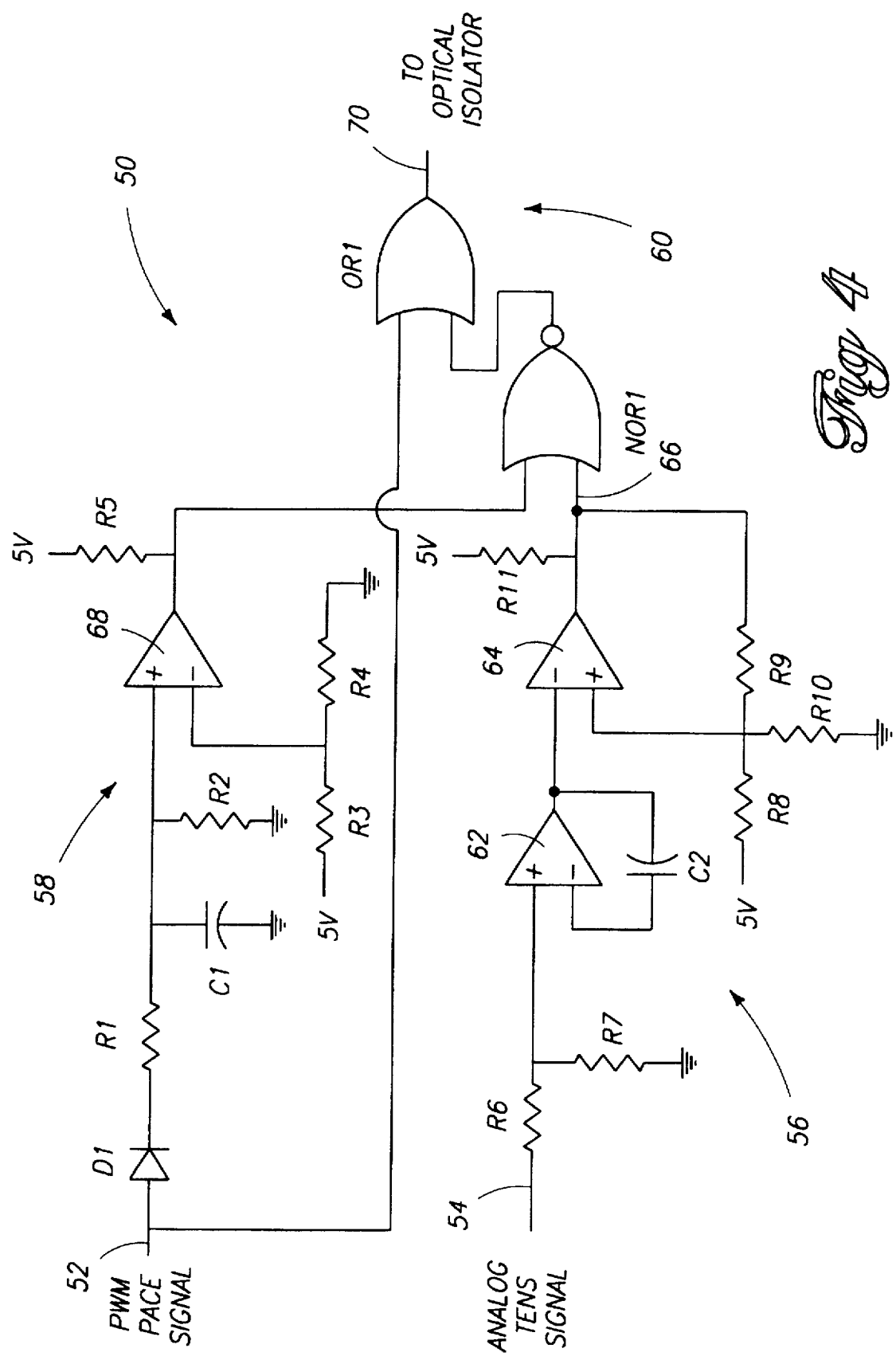
FIG. 4 is a schematic of a circuit employed in the transcutaneous cardiac pacing system to coordinate pacing pulses with nerve stimulation pulses according to a second implementation.

FIG. 4 shows a schematic of a pacer board circuit 50 which can be implemented as the coordinating device 42 of grounded circuitry 32 in FIG. 2. This pacer board circuit 50 represents a slightly different and alternative implementation from the FIG. 2 implementation in that the microprocessor 40 does not generate a pulse width modulated TENS signal. Instead, in this second implementation, a separate external signal generator (not shown) is used to generate an analog TENS signal. The external signal generator sets the frequency, pulse width, and amplitude of the analog TENS signal. Such signal generators are well-known and not described in detail. The microprocessor 40 does produce, however, the PWM pacing signal in the conventional manner of the Codemaster defibrillator system. One feature of this second implementation is that the microprocessor 40 need not be reprogrammed to generate a PWM TENS signal.

The PWM pacing signal and the analog TENS signal are supplied at inputs 52 and 54, respectively. The pacer board circuit 50 includes an analog-to-PWM converter 56, a gating device 58, and a summing device 60. The analog-to-PWM converter 56 converts the nerve stimulation signal from a non-modulated analog signal to a pulse width modulated signal. The analog-to-PWM converter 56 includes an operational amplifier 62 and a comparator 64 which produce a PWM TENS signal at output 66.

The gating device 58 is designed to disable output of the PWM TENS pulse at output 66 during a PWM pacing pulse.

The gating device 58 includes a peak detection circuit (resistors R1 and R2, and capacitor C1) which detects when a pacing pulse is occurring, a comparator 68, and a NOR gate NOR1. In the illustrated implementation, the comparator 68 outputs an asserted high signal (e.g., a binary "1") during a pacing pulse and an asserted low signal (e.g., a binary "0") in the absence of a pacing pulse. The NOR gate NOR1 outputs the PWM TENS signal only it receives the asserted low signal from comparator 68. The summing device 60 comprises an OR gate OR1 which is coupled to receive the PWM pacing signal and the output of the NOR gate NOR1.

According to this arrangement, when a pacing pulse is received at input 52, the gating device 58 prevents output of the PWM TENS signal 66. Only the PWM is pacing signal is received and output by the summing device 60 to the optical isolator. Conversely, in the period between pacing pulses, the gating device 58 passes the PWM TENS signal 66 onto the summing device 60 for output to the optical isolator. An output 70 of the pacer board circuit 50 therefore provides a composite PWM signal consisting of the pacing signal and the TENS signal.

Figure 5:
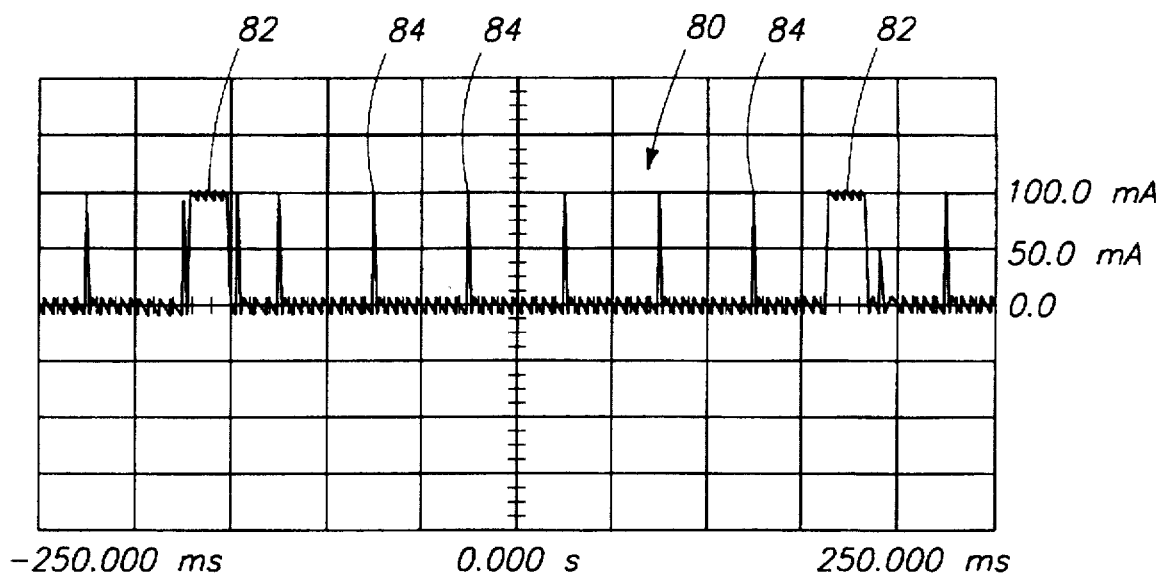
FIG. 5 is a waveform representation of the pacing pulses and nerve stimulation pulses.

FIG. 5 shows the composite PWM signal 80 generated by pacer board circuit 50. The PWM signal 80 consists of a series of pacing pulses 82 to stimulate cardiac activity and one or more intermittent nerve stimulation pulses 84 interjected between successive pacing pulses to mitigate pain or discomfort. Each horizontal grid division represents 50 ms and each vertical grid division represents 50 mA. The pacing pulses 82 are periodically generated and applied at a rate of about 180 pulses per minute (i.e., one pulse every 333 ms). Each TP pulse 82 has a duration of approximately 18–20 ms and an amplitude of approximately 100 mA. Multiple nerve stimulation pulses 84 are interposed between the pacing pulses at a rate of about 40 Hz (i.e., one pulse every 50 ms). Each TENS pulse 84 has a duration of approximately 100–500 µs and an amplitude of approximately 90–100 mA.

Figure 6:
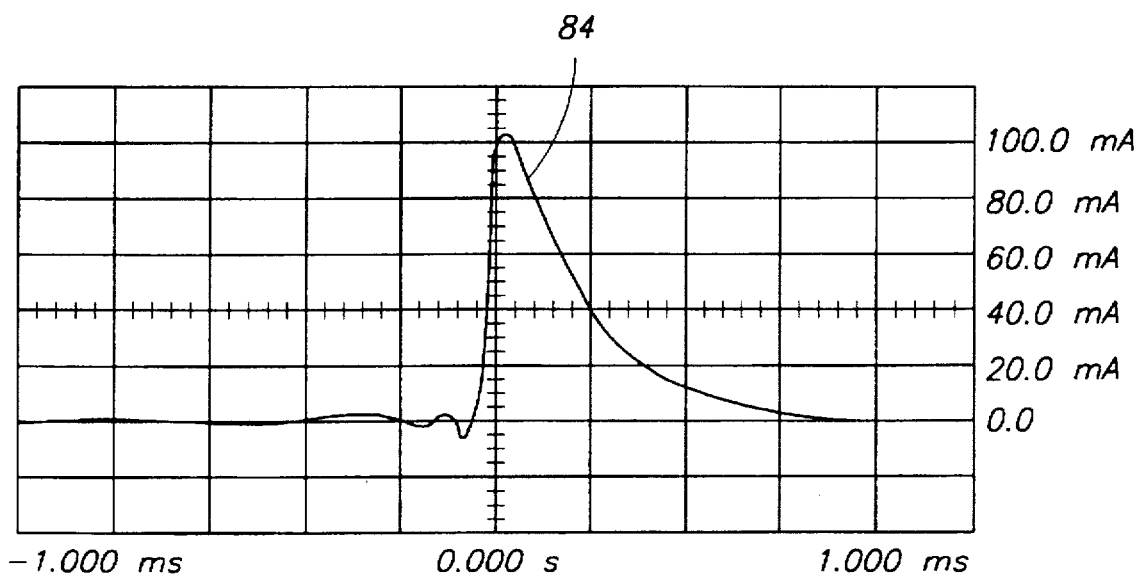
FIG. 6 is a waveform representation of a single nerve stimulation pulse at a different resolution than that shown in FIG. 5.

FIG. 6 shows a single TENS pulse 84 in more detail. Here, each horizontal grid division represents 200 µs and each vertical grid division represents 20 mA. The TENS pulse has a rapid onset, followed by an exponential decay.

It is noted that the TENS pulses and the TP pulses might be applied through two different sets of electrodes. In this case, the circuitry is modified to have two outputs, two optical couplers, and two patient-isolate circuits which apply the signals separately to the two sets of electrodes.

The system and method described herein effectively reduce pain experienced by the patient during administration of transcutaneous pacing through coordinated and concurrent use of transcutaneous nerve stimulation. The system and method are advantageous in that they reduce or eliminate use of intravenous drugs and sedation.

In compliance with the statute, the invention has been described in language more or less specific as to structure and method features. It is to be understood, however, that the invention is not limited to the specific features described, since the means herein disclosed comprise exemplary forms of putting the invention into effect. The invention is, therefore, claimed in any of its forms or modifications within the proper scope of the appended claims appropriately interpreted in accordance with the doctrine of equivalents and other applicable judicial doctrines.

We claim:

1. A method for administering cardiac pacing comprising the following steps:

applying transcutaneous pacing to a patient to stimulate cardiac activity; and applying transcutaneous electrical nerve stimulation to the patient concurrently with application of said transcutaneous pacing to mitigate discomfort in the patient.

2. A method as recited in claim 1, wherein:

said step of applying transcutaneous pacing comprises applying a series of pacing pulses; and said step of applying transcutaneous electrical nerve stimulation comprises intermittently applying one or more nerve stimulating pulses between application of said pacing pulses.

3. A method as recited in claim 2, further comprising the following additional steps:

applying said pacing pulses through a set of electrodes attached to the patient; and applying said nerve stimulating pulses through the set of electrodes attached to the patient.

4. A method as recited in claim 2, further comprising the following additional steps:

applying said pacing pulses through a first set of electrodes attached to the patient; and applying said nerve stimulating pulses through a different second set of electrodes attached to the patient.

5. A method as recited in claim 1, wherein:

said step of applying transcutaneous pacing comprises generating pacing pulses of a first pulse duration; and said step of applying transcutaneous electrical nerve stimulation comprises generating nerve stimulating pulses of a second pulse duration shorter than the first pulse duration.

6. A method as recited in claim 5, wherein the first pulse duration is in an approximate range of 18–20 ms and the second pulse duration is in an approximate range of 100–500 µs.

7. A transcutaneous cardiac pacing system comprising:

a set of electrodes adapted for attachment to a cutaneous layer of a patient;

a transcutaneous pacing system coupled to supply pacing pulses to the patient via the set of electrodes, the pacing pulses being effective to stimulate cardiac activity in the patient; and a transcutaneous electrical nerve stimulation system coupled to supply nerve stimulation pulses to the patient via the set of electrodes, the nerve stimulation pulses being effective to mitigate discomfort in the patient.

8. A transcutaneous cardiac pacing system as recited in claim 7 wherein:

the transcutaneous pacing system includes means for permitting an administrator to dynamically adjust control parameters of the pacing pulses; and the transcutaneous electrical nerve stimulation system includes means for permitting the administrator to dynamically adjust control parameters of the nerve stimulation pulses.

9. A transcutaneous cardiac pacing system as recited in claim 7, wherein the set of electrodes form a first set of electrodes further, comprising:

a second set of electrodes adapted for attachment to the cutaneous layer of the patient;

the transcutaneous pacing system being coupled to the first set of electrodes to supply pacing pulses to the patient via the first set of electrodes; and the transcutaneous electrical nerve stimulation system being coupled to the second set of electrodes to supply the nerve stimulation pulses to the patient via the second set of electrodes.

10. A transcutaneous cardiac pacing system as recited in claim 7 further comprising means for coordinating the pacing pulses supplied by the transcutaneous pacing system and the nerve stimulation pulses supplied by the transcutaneous electrical nerve stimulation system so that one or more nerve stimulation pulses are supplied between successive pacing pulses.

11. A transcutaneous cardiac pacing system as recited in claim 7 further comprising a coordinating device to form a single pulse string consisting of the pacing pulses and the nerve stimulation pulses for output to the set of electrodes.

12. A transcutaneous cardiac pacing system as recited in claim 7 wherein the transcutaneous pacing system and the transcutaneous electrical nerve stimulation system have means for forming the pacing pulses and the nerve stimulation pulses using pulse width modulation.

13. A transcutaneous cardiac pacing system as recited in claim 7 wherein:
the pacing pulses have a pulse duration in a range of approximately 18–20 ms; and
the nerve stimulation pulses have a pulse duration in a range of approximately 100–500 μs.

14. A cardiac pacing system comprising:
a transcutaneous pacing generator to generate a pacing signal;
a transcutaneous electrical nerve stimulation generator to generate a nerve stimulation signal; and
coordinating circuitry connected to the transcutaneous pacing generator and the transcutaneous electrical nerve stimulation generator to coordinate output of the pacing signal and the nerve stimulation signal.

15. A cardiac pacing system as recited in claim 14 wherein the transcutaneous pacing generator generates a pulse width modulated pacing signal.

16. A circuit for use in a cardiac pacing system, the circuit comprising:
a first input to receive a pacing signal;
a second input to receive a non-modulate, analog nerve stimulation signal;
at least one output to output at least one of the pacing signal or the nerve stimulation signal;
an analog-to-PWM converter coupled to the second input to convert the nerve stimulation signal from a non-modulated analog signal to a pulse width modulated signal; and coordinating circuitry connected between the inputs and the output to coordinate output of the pacing signal and the nerve stimulation signal.

17. A cardiac pacing system as recited in claim 14 wherein:
the transcutaneous pacing generator generates a pacing signal that is pulse width modulated;
the transcutaneous electrical nerve stimulation generator generates a nerve stimulation signal that is pulse width modulated; and
the coordinating circuitry comprises a summing device to combine the pacing signal and the nerve stimulation signal into a single output signal consisting of pacing pulses and nerve stimulation pulses.

18. A cardiac pacing system as recited in claim 14 wherein:
the transcutaneous pacing generator generates a pacing signal that is pulse width modulated;
the transcutaneous electrical nerve stimulation generator generates a nerve stimulation signal that is pulse width modulated; and
the coordinating circuitry is configured to simultaneously output the pacing signal and the nerve stimulation signal.

19. A cardiac pacing system as recited in claim 18, further comprising:
first and second outputs connected to the coordinating circuitry, the first output being connected to output the pacing signal and the second output being connected to output the nerve stimulation signal.

20. A cardiac pacing system as recited in claim 14 wherein:
the transcutaneous pacing generator generates a pacing signal that is pulse width modulated;
the transcutaneous electrical nerve stimulation generator generates a nerve stimulation signal that is pulse width modulated; and
the coordinating circuitry includes a gating device to alternately output the pacing signal or the nerve stimulation signal.

* * * * *